(12) United States Patent
Vija et al.

(10) Patent No.: US 11,701,067 B2
(45) Date of Patent: Jul. 18, 2023

(54) ATTENUATION CORRECTION-BASED WEIGHTING FOR TOMOGRAPHIC INCONSISTENCY DETECTION

(71) Applicant: Siemens Medical Solutions USA, Inc., Malvern, PA (US)

(72) Inventors: Alexander Hans Vija, Evanston, IL (US); Francesc dAssis Massanes Basi, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 13 days.

(21) Appl. No.: 17/447,118

(22) Filed: Sep. 8, 2021

(65) Prior Publication Data
US 2023/0076112 A1    Mar. 9, 2023

(51) Int. Cl.
*A61B 6/03* (2006.01)
*A61B 6/00* (2006.01)

(52) U.S. Cl.
CPC .......... *A61B 6/037* (2013.01); *A61B 6/4258* (2013.01); *A61B 6/466* (2013.01); *A61B 6/469* (2013.01); *A61B 6/5264* (2013.01)

(58) Field of Classification Search
CPC ....... A61B 6/037; A61B 6/4258; A61B 6/466; A61B 6/469; A61B 6/5264
See application file for complete search history.

(56) References Cited

U.S. PATENT DOCUMENTS

| | | |
|---|---|---|
| 8,577,103 B2 | 11/2013 | Vija et al. |
| 8,675,936 B2 | 3/2014 | Vija et al. |
| 9,332,907 B2 | 5/2016 | Vija |

(Continued)

OTHER PUBLICATIONS

Kim, Kyungsang et al: "Data-driven respiratory gating based on localized diaphragm sensing in TOF PET", Physics in Medicine and Biology, Institute of Physics Publishing, Bristol GB, vol. 65, No. 16, Aug. 13, 2020 (Aug. 13, 2020), p. 165007, XP020355792, ISSN: 0031-9155, DOI: 10.1088/1361-6560/AB9660 [retrieved on Aug. 13, 2020].

(Continued)

*Primary Examiner* — Marcus H Taningco

(57) ABSTRACT

A system and method includes determination of a region of interest of an imaging subject, generation of a first linear attenuation coefficient map of the imaging subject, the first linear attenuation coefficient map generated to associate voxels of the region of interest of the imaging subject with greater linear attenuation coefficients than voxels of other regions of the imaging subject, attenuation-correction of a plurality of tomographic frames of the imaging subject based on the first linear attenuation coefficient map to generate a second plurality of tomographic frames, and determination of tomographic inconsistency of the second plurality of tomographic frames. Some aspects further include generation of a second linear attenuation coefficient map of the imaging subject, attenuation-correction of the plurality of tomographic frames based on the second linear attenuation coefficient map to generate a third plurality of tomographic frames, and reconstruction of a three-dimensional image based on the third plurality of tomographic frames and the determined tomographic inconsistency.

17 Claims, 6 Drawing Sheets

(56) References Cited

U.S. PATENT DOCUMENTS

| | | |
|---|---|---|
| 10,304,219 B2 | 5/2019 | Cachovan et al. |
| 10,699,445 B2 | 6/2020 | Vija et al. |
| 2012/0155733 A1* | 6/2012 | Wagenkenecht ...... G06T 11/005 382/131 |
| 2015/0289832 A1* | 10/2015 | Bal ...................... A61B 6/5264 600/407 |
| 2016/0327622 A1* | 11/2016 | Ahn .................... G01R 33/481 |
| 2020/0100752 A1* | 4/2020 | Morita ................. A61B 6/5264 |

OTHER PUBLICATIONS

Van Den Hoff J. et al: "Motion Compensation in Emission Tomography" In: "Handbook of Particle Detection and Imaging", 2020, Springer International Publishing, Chaco, XP093015936, ISBN: 978-3-319-47999-6 pp. 1-47, DOI: 10.1007/978-3-319-47999-6_40-2, Retrieved from the Internet: URL:http://link.springer.com/content/pdf/10.1007/978-3-319-47999-6_40-2> * p. 9 * * p. 38-p. 42 *.

* cited by examiner

ATTENUATION CORRECTION-BASED WEIGHTING FOR TOMOGRAPHIC INCONSISTENCY DETECTION

BACKGROUND

According to conventional nuclear imaging, a radiopharmaceutical is introduced into a patient body by injection or ingestion. The radiopharmaceutical emits gamma rays (in the case of single-photon-emission-computer-tomography (SPECT) imaging) or positrons which annihilate with electrons to produce gamma rays (in the case of positron-emission-tomography (PET) imaging). A detector system located outside the body detects the emitted gamma rays (i.e., acquires event data) and reconstructs images based thereon.

Detection of the emitted gamma rays occurs over a period of time, during which the body may move, either inadvertently or due to natural physiological processes such as respiration and heartbeat. Such movement can lead to tomographic inconsistency, which may be visually detectable in the projection data, particularly in the brain, abdominal, thoracic and cardiac regions. Some systems address the foregoing by systems detecting patient movement and correcting acquired event data based on the detected movement. The detected movement may be recorded as motion vectors occurring at particular times during the data acquisition. The motion vectors may then be used to correct the acquired data prior to image reconstruction.

Recent systems attempt to detect motion by registering the nuclear data against data contemporaneously acquired by a more motion-robust imaging modality (e.g., computed tomography (CT)). However, such systems require two independent imaging systems. Other recent systems attempt to detect motion by comparing the acquired data against a system data model which models acquisition parameters of the nuclear imaging system. This comparison may produce unsatisfactory results because detection of and correction for motion of one region within the field of view (e.g., the jaw) may unnecessarily blur the image of the actual region of interest (ROI) (e.g., the brain) which may have remained relatively motionless during the acquisition.

Improved systems for correcting tomographic inconsistency within a region of interest of tomographic data are desired.

DETAILED DESCRIPTION

The following description is provided to enable any person in the art to make and use the described embodiments and sets forth the best mode contemplated for carrying out the described embodiments. Various modifications, however, will remain apparent to those in the art.

A linear attenuation coefficient represents the probability that a photon will undergo an interaction while passing through a unit thickness of tissue. A typical mu-map endeavors to accurately represent these probabilities within a volume by assigning a corresponding linear attenuation coefficient to each voxel based on the tissue characteristics within the voxel. Attenuation correction corrects acquired emission data based on such a mu-map so that the attenuation-corrected emission data shows quantitatively-accurate activity (e.g., tracer uptake in Bq/ml) within each voxel.

In contrast, embodiments utilize the mu-map/attenuation correction paradigm to perform a task other than production of quantitatively-accurate emission data. For example, some embodiments apply attenuation correction to emission data using an ROI-emphasizing linear attenuation coefficient map in order to emphasize (e.g., increase the relative brightness) of voxels of an ROI (e.g., the heart) and/or de-emphasize (e.g., decrease the relative brightness) of non-ROI voxels. The thusly-emphasized emission data is then analyzed to determine tomographic inconsistency. The determination of tomographic inconsistency is therefore driven by the voxels of the ROI to a greater extent than it would be if attenuation correction had been performed using a physically representative linear attenuation coefficient map. The ROI-emphasizing linear attenuation coefficient map may be generated based on the emission data, a test reconstruction, operator input, and/or data of a second imaging modality.

Once the task (e.g., determination of tomographic inconsistency) has been completed, the original emission data may be attenuation-corrected using a physically-representative linear attenuation coefficient map. Further to the above example, an image may be reconstructed from this attenuation-corrected emission data using correction information derived from the determined tomographic inconsistency. Some embodiments may therefore facilitate efficient ROI-relevant correction of attenuation-corrected emission data.

Figure 1:
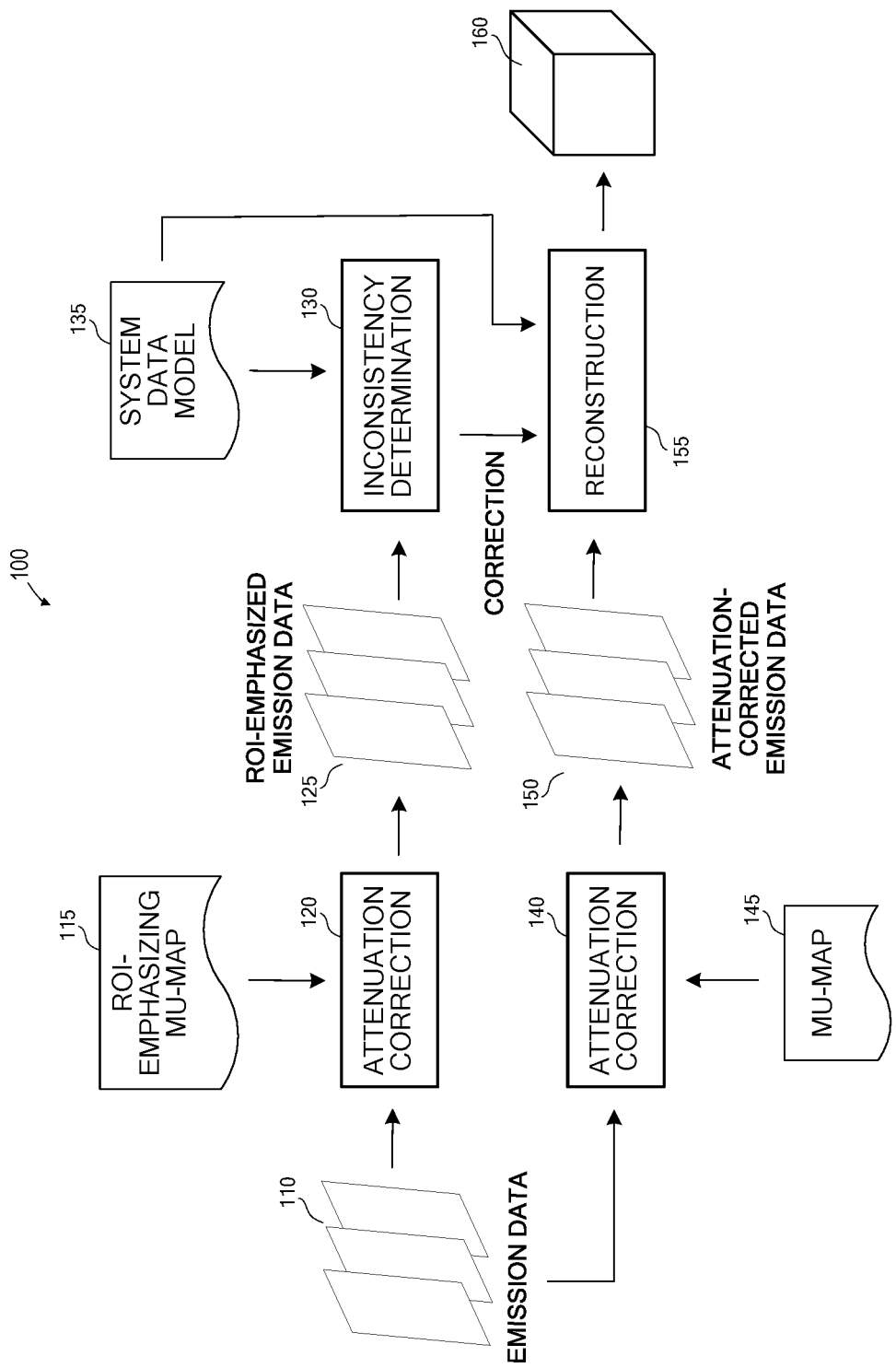
FIG. 1 is a block diagram of a system to determine tomographic inconsistency of emission data by attenuation-correcting the emission data using an ROI-emphasizing linear attenuation coefficient map and to reconstruct an image based on the determined tomographic inconsistency and the emission data according to some embodiments.

FIG. 1 illustrates system 100 according to some embodiments. Each component of system 100 and each other component described herein may be implemented using any combination of hardware and/or software. Some components may share hardware and/or software of one or more other components.

Emission data 110 may comprise a plurality of two-dimensional projection images representing radioactivity within a subject as is known in the art. For example, a radioactive tracer is injected into a patient and a SPECT detector rotates around a patient to receive gamma ray emissions therefrom over a prescribed period of time at each of a plurality of projection angles. Each projection image of emission data 110 indicates a degree of radioactivity (e.g., via pixel brightness) emitted from various spatial locations of the patient.

ROI-emphasizing mu-map 115 specifies linear attenuation coefficients for each voxel of the subject volume. In contrast to a typical mu-map as described above, ROI-emphasizing mu-map 115 is intended to attenuate activity which does not emanate from the ROI (e.g., via increasing the linear attenuation coefficients of those voxels which are not within the ROI) such that, after application of attenuation correction using mu-map 115, those voxels appear brighter than they would appear if a mu-map which accurately represents the photon density of each voxel were used. Benefits of such an arrangement will become apparent from the description below.

According to some embodiments, ROI-emphasizing mu-map 115 may be generated by initially generating a mu-map of the subject volume using any techniques that are known in the art. This mu-map is then modified to increase the linear attenuation coefficients of those voxels which are not within the ROI. The ROI may be identified in any number of ways. For example, a fast, low-quality reconstruction of emission data 110 may be performed to generate slice images for presentation to an operator. The operator may then indicate the ROI within the slice images as will be described in more detail with respect to FIG. 5. In other embodiments, CT data of the volume is obtained and segmented to automatically or semi-automatically identify an organ of interest.

In still other embodiments, the ROI may be determined directly from emission data 110. For example, in a case that emission data 110 were acquired using a focusing collimator set to focus on the ROI, the ROI could be identified by identifying the region in which the detected counts are concentrated. Another method for determining the ROI directly from image data will be described in more detail with respect to FIG. 4.

Attenuation correction component 120 applies attenuation correction to emission data 110 based on mu-map 115. Attenuation correction component 120 may implement any attenuation correction algorithm that is or becomes known. As a result of attenuation correction using mu-map 115, voxels of the ROI of resulting ROI-emphasized emission data 125 appear brighter than they would appear if a mu-map including physically-accurate linear attenuation coefficients were used.

Next, inconsistency determination component 130 determines the tomographic inconsistency of ROI-emphasized emission data 125 based on system data model 135. As is known in the art, system data model 135 models the data acquisition of the system which acquired emission data 110. Accordingly, inconsistency determination component 130 may determine whether ROI-emphasized emission data 125 is consistent with the modeled data acquisition.

Inconsistency determination component 130 also outputs correction information which may be used to correct any determined inconsistencies. The correction information may comprise shift vectors which indicate an extent to which each projection image of emission data 110 should be shifted (e.g., in X, Y directions) in order to correct the inconsistencies. The correction information may include more than one shift vector for each projection image (e.g., one shift vector for each of several different regions) according to some embodiments.

The determination of tomographic inconsistency gives more weight to brighter voxels of input emission data. Accordingly, by increasing the relative brightness of the voxels of the ROI using mu-map 115, embodiments efficiently bias the determination of tomographic inconsistency and the resulting correction information, toward improving the image quality of the ROI.

Elements 140 through 160 of FIG. 1 represent optional additional processing according to some embodiments. Attenuation correction component 140 applies attenuation correction to mission data 110 based on mu-map 145 to generate attenuation-corrected emission data 150. Mu-map 145 is a "traditional" mu-map representing the expected, predicted and/or actual linear attenuation coefficients of the voxels represented in emission data 110. Attenuation correction component 140 may execute the same or a different attenuation correction algorithm as attenuation correction component 120. Accordingly, attenuation correction component 120 and attenuation correction component 140 may be implemented by a same component.

Reconstruction component 155 reconstructs three-dimensional image 160 based on attenuation-corrected emission data 150, the correction information generated by inconsistency determination component 130, and system data model 135. Such reconstruction algorithms are known in the art and may take into account shift vectors if such vectors are included in the correction information generated by inconsistency determination component 130. Image 160 may then be displayed as a three-dimensional view, a slice view, and/or any other suitable view. Due to the use of mu-map 115 for inconsistency correction and mu-map 145 for attenuation correction, image 160 includes both quantitative data (e.g., Bq/ml) and improved quality within the ROI.

Some embodiments do not include elements 140, 145 and 150 of FIG. 1. Instead, reconstruction component 155 reconstructs three-dimensional image 160 based on ROI-emphasized emission data 125, the correction information generated by inconsistency determination component 130, and system data model 135. An operator may determine whether to perform reconstruction using ROI-emphasized emission data 125 or attenuation-corrected emission data 150.

Figure 2:
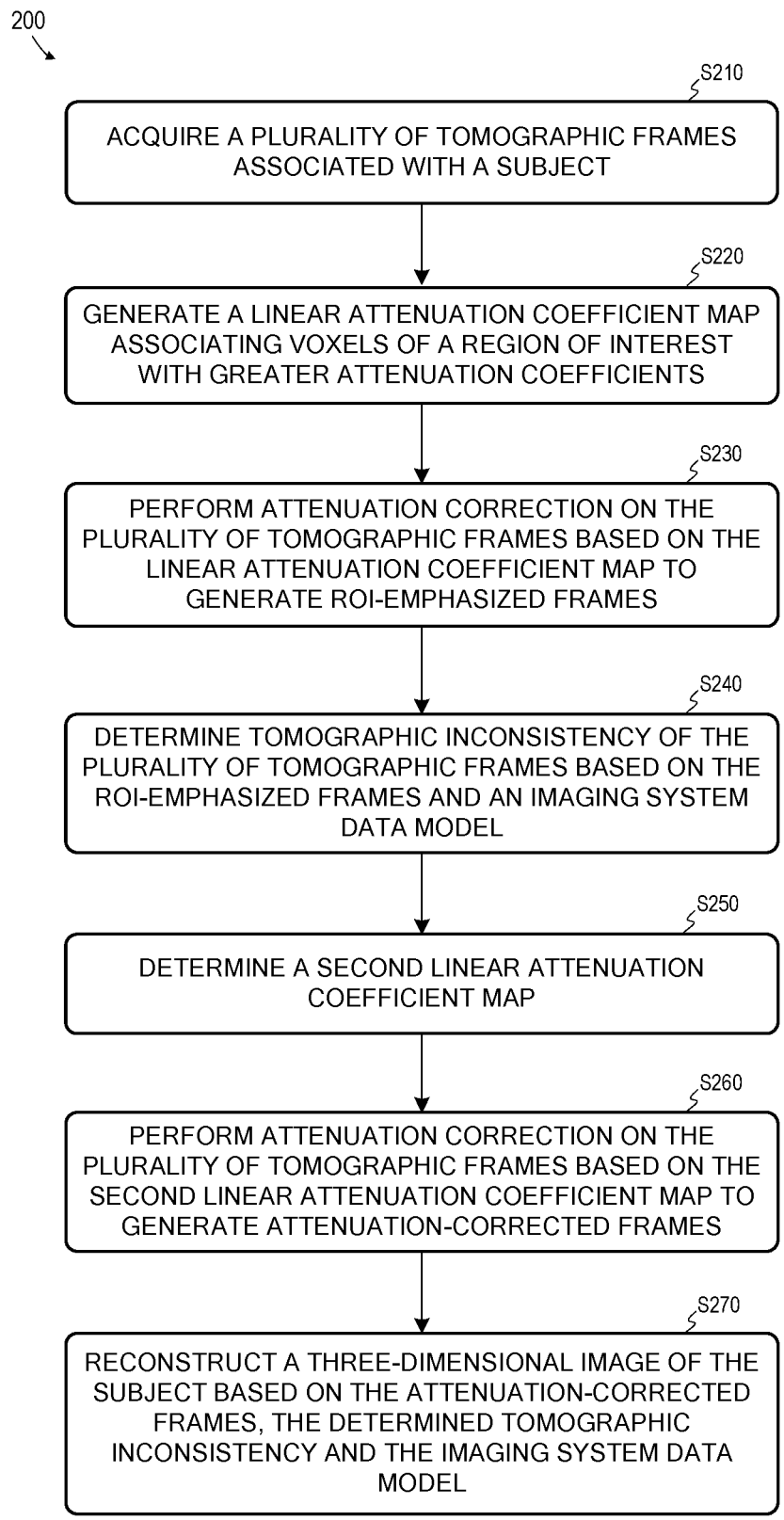
FIG. 2 is a flow diagram of a process to determine tomographic inconsistency of emission data by attenuation-correcting the emission data using an ROI-emphasizing linear attenuation coefficient map and to reconstruct an image based on the determined tomographic inconsistency and the emission data according to some embodiments.

FIG. 2 comprises a general flow diagram of process 200 according to some embodiments. Process 200 may be executed by system 100, but embodiments are not limited thereto. In some embodiments, various hardware elements (e.g., one or more processing units) execute program code to perform process 200. The steps of process 200 need not be performed by a single device or system, nor temporally adjacent to one another or in the order shown.

Process 200 and all other processes mentioned herein may be embodied in processor-executable program code read from one or more non-transitory computer-readable media, such as a disk-based or solid-state hard drive, a DVD-ROM, a Flash drive, and a magnetic tape, and then stored in a compressed, uncompiled and/or encrypted format. In some embodiments, hard-wired circuitry may be used in place of, or in combination with, program code for implementation of processes according to some embodiments. Embodiments are therefore not limited to any specific combination of hardware and software.

Initially, at S210, a plurality of tomographic frames associated with a subject are acquired. The frames may be acquired at S210 using any imaging modality which generates tomographic data, including but not limited to SPECT, PET and CT.

Figure 3:
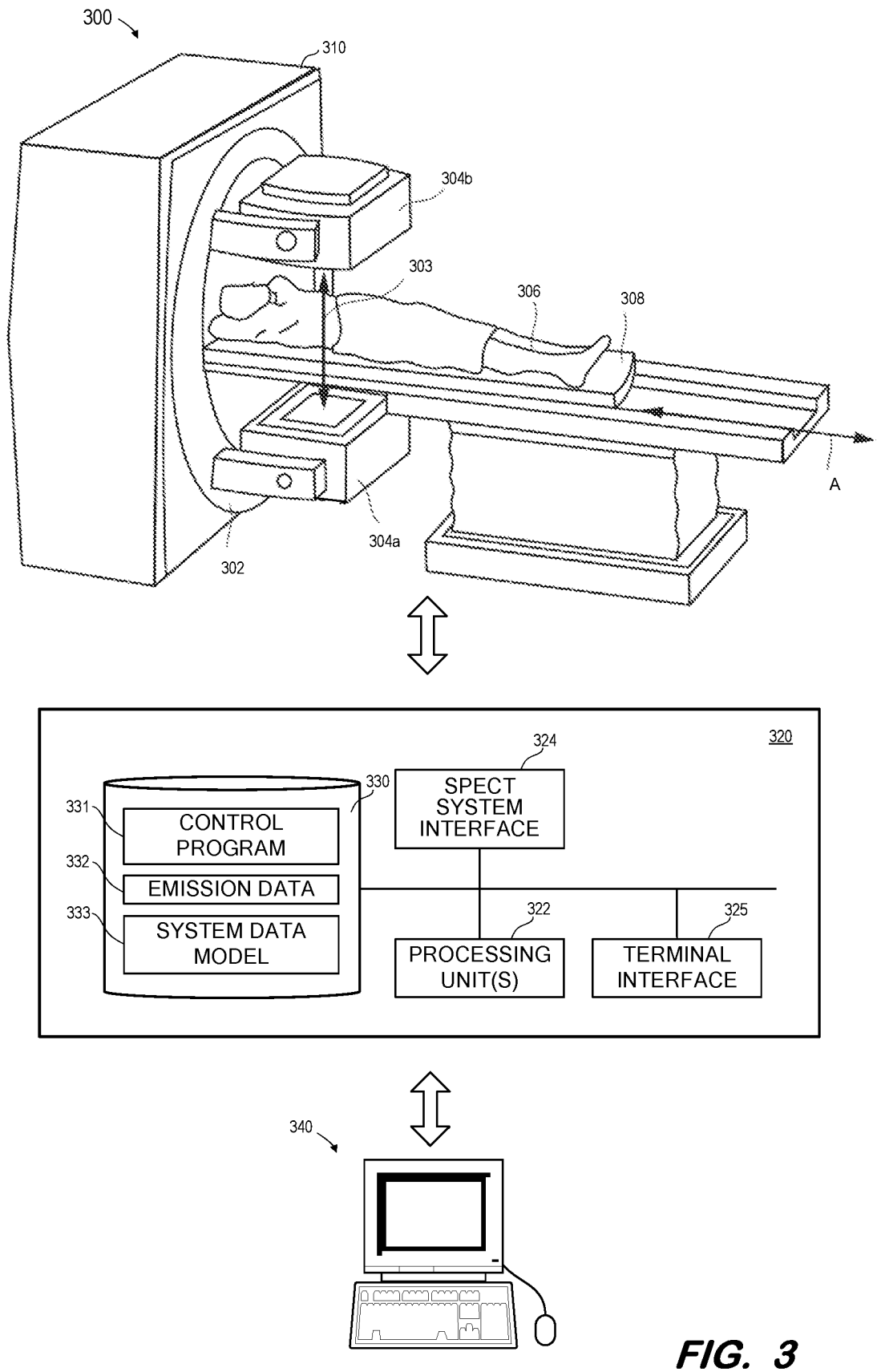
FIG. 3 illustrates a SPECT imaging system according to some embodiments.

FIG. 3 illustrates system 300 which may be used to acquire frames at S210 and perform various other steps of process 200 according to some embodiments. According to some embodiments, the plurality of tomographic frames are acquired by an imaging device prior to S210, and S210 simply consists of retrieving the already-acquired images from storage. System 300 is a SPECT imaging system as is known in the art, but embodiments are not limited thereto. Each of component of system 300 may include other elements which are necessary for the operation thereof, as well as additional elements for providing functions other than those described herein.

System 300 includes gantry 302 to which two or more gamma cameras 304a, 304b are attached, although any number of gamma cameras can be used. A detector within each gamma camera detects gamma photons (i.e., emission data) 303 emitted by a radioactive tracer injected into the body of patient 306 lying on bed 308. Bed 308 is slidable along axis-of-motion A. At respective bed positions (i.e., imaging positions), a portion of the body of patient 306 is positioned between gamma cameras 304a, 304b in order to capture emission data from that body portion from various projection angles.

Control system 320 may comprise any general-purpose or dedicated computing system. Control system 320 includes one or more processing units 322 configured to execute processor-executable program code to cause system 320 to operate as described herein, and storage device 330 for storing the program code. Storage device 330 may comprise one or more fixed disks, solid-state random access memory, and/or removable media (e.g., a thumb drive) mounted in a corresponding interface (e.g., a USB port).

Storage device 330 stores program code of control program 331. One or more processing units 322 may execute control program 331 to, in conjunction with SPECT system interface 324, control motors, servos, and encoders to cause gamma cameras 304a, 304b to rotate along gantry 302 and to acquire two-dimensional emission data 332 at defined imaging positions during the rotation. System data model 333 models the imaging parameters of system 300 and is used during reconstruction as is known in the art.

Terminal 340 may comprise a display device and an input device coupled to system 320. Terminal 340 may receive and display tomographic images and/or preliminarily- or fully-reconstructed images, and may receive operator input specifying an ROI or for otherwise controlling operation of imaging system 300. In some embodiments, terminal 340 is a separate computing device such as, but not limited to, a desktop computer, a laptop computer, a tablet computer, and a smartphone.

A linear attenuation coefficient map is generated at S220. The linear attenuation coefficient map specifies linear attenuation coefficients for each voxel of the subject volume. Unlike a traditional map, the generated linear attenuation coefficient map is intended to assign greater linear attenuation coefficients to voxels which do not lie within an ROI.

The ROI may be determined in any suitable manner. In some embodiments, an image is reconstructed from the acquired frames and the image is displayed to an operator, who uses an input device to define an ROI within the image. In other embodiments, projection images of a contemporaneous CT scan are reconstructed and the resulting image is segmented to identify different regions therein. An operator may then specify an organ, for example, within the segmented CT data as the ROI. Some embodiments acquire projection images using focused collimation such that sensitivity to activity within a particular region is higher than within other regions. Accordingly, an ROI might be determined at S220 by identifying a region which exhibits the greatest activity.

Figure 4:
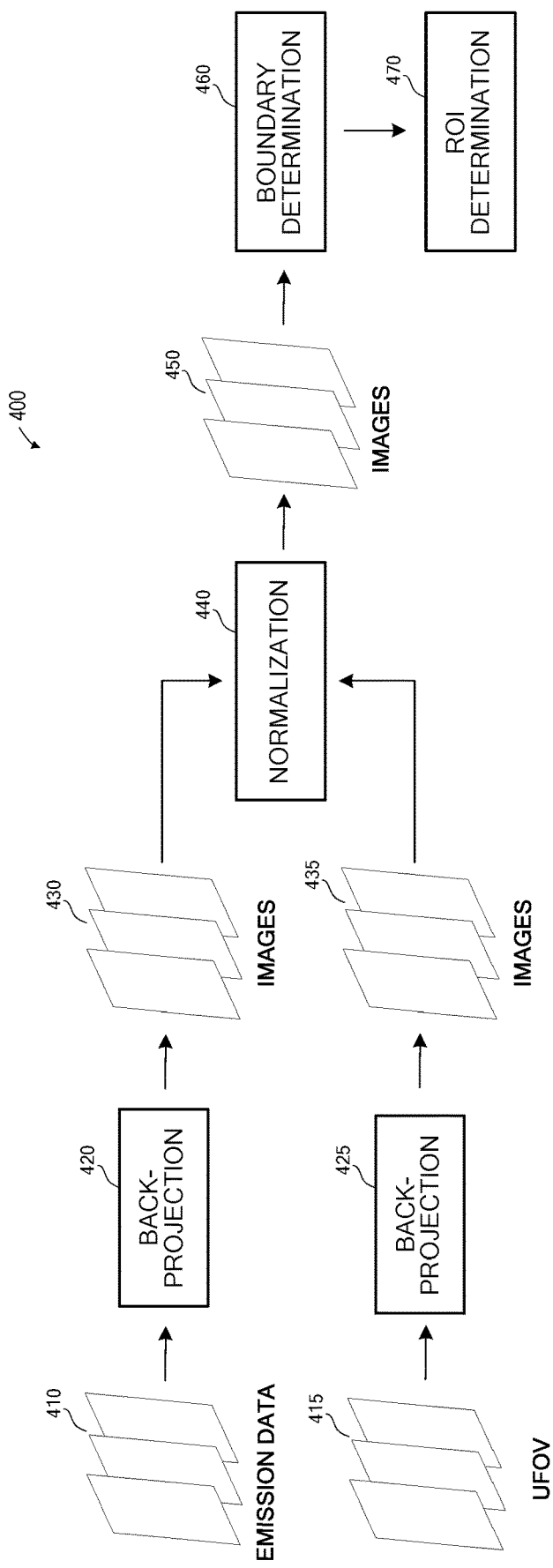
FIG. 4 is a block diagram illustrating determining an ROI based on nuclear data according to some embodiments.

FIG. 4 illustrates system 400 to determine an ROI at S220 from nuclear emission data according to some embodiments. Emission data 410, acquired at S210, may specify a number of photons received at each pixel of a SPECT camera for each projection angle. Projection data 415, representing the useful field of view (UFOV) of the imaging system, are acquired from each of the projection angles without the presence of any object in the field of view. Back-projection algorithms 420 and 425 are applied to each of data 410 and 415 to generate respective images 430 and 435.

Images 435 are used to normalize images 430, resulting in images 450. From images 450, which represent views of the subject from each of respective projection angles, boundary determination component 460 may estimate a three-dimensional outer boundary of the subject. For example, in the case of a human subject, the three-dimensional outer boundary may roughly comprise an ellipsoid.

ROI determination component 470 determines an ROI from the determined outer boundary. For example, in a case that the ROI is intended to include the heart, ROI determination component 470 may define an axial section of the ellipsoid as the ROI based on an estimated relationship between the location of the heart region and the two ends of the ellipsoid.

Regardless of how the ROI is determined, the map generated at S220 may associate voxels of the ROI with smaller linear attenuation coefficients than surrounding voxels. In some embodiments of S220, a linear attenuation coefficient map of the subject volume is generated using any techniques that are known in the art and is then modified to increase the linear attenuation coefficients of voxels not located within the ROI.

Figure 5:
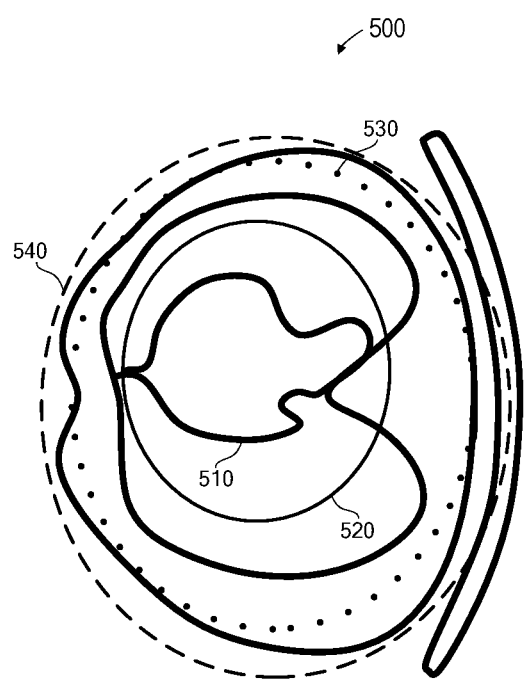
FIG. 5 depicts a slice image including ROI notations for generating an ROI-emphasized linear attenuation coefficient map according to some embodiments.

FIG. 5 is a depiction of a slice image to illustrate a linear attenuation map generated at S220 according to some embodiments. The thickest lines outline anatomical features, including heart region 510. Ellipses 520, 530 and 540 are used to define different ranges of linear attenuation coefficients. Assuming the heart is the ROI, linear attenuation coefficients of voxels within ellipse 520 are set to a lowest value, linear attenuation coefficients of voxels within ellipse 530 and not within ellipse 520 are set to a greater value, and linear attenuation coefficients of voxels within ellipse 540 and not within ellipse 530 are set to an even greater value.

Each ellipse need not be associated with a same linear attenuation coefficient in some embodiments. Any scheme for increasing the linear attenuation coefficients of certain voxels in comparison to other voxels may be employed. For example, each ellipse may be associated with a multiplier in some embodiments such that linear attenuation coefficients of voxels within ellipse 520 are set to one-tenth their "true" value, linear attenuation coefficients of voxels within ellipse 530 and not within ellipse 520 are set to half their true value, and linear attenuation coefficients of voxels within ellipse 540 and not within ellipse 530 are set to three times their true value.

Attenuation correction is performed on the acquired frames at S230 based on the map generated at S220 to generate ROI-emphasized frames. Attenuation correction at S230 may proceed using any attenuation correction algorithm that is or becomes known. Due to the use of the map generated at S220, voxels of the ROI appear brighter in the ROI-emphasized frames than they would appear using a traditional linear attenuation coefficient map.

Figure 6:
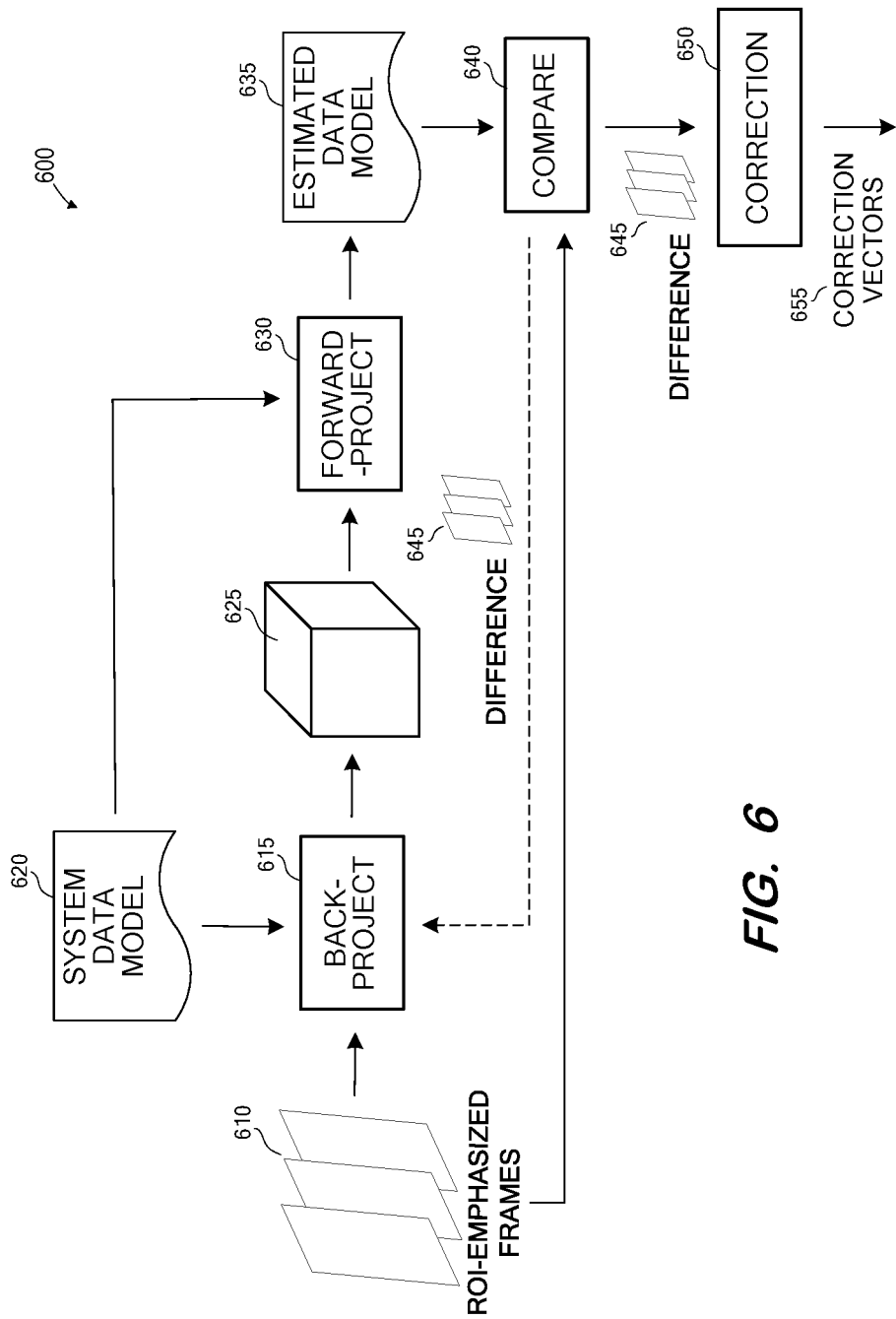
FIG. 6 is a block diagram of a system to determine shift vectors based on emission data attenuation-corrected using an ROI-emphasizing linear attenuation coefficient map according to some embodiments.

The tomographic inconsistency of the frames acquired at S210 is determined at S240 based on the ROI-emphasized frames and on a data model (or system matrix) of an imaging system which was used to acquire the tomographic frames. FIG. 6 illustrates system 600 to determine tomographic inconsistency according to some embodiments. As depicted, ROI-emphasized frames 610 are back-projected by component 615 using system data model 620 to generate three-dimensional image 625. Image 630 is then forward-projected by component 630 using data model 620 to generate estimated data model 635. Frames 610 are compared against estimated data model 635 by component 640 to generate difference frames 645.

The dashed line of FIG. 6 indicates optional iterations which may be employed to refine difference frames 645. During such an iteration, difference frames are back-projected to generate an updated image 625, which is forward-projected to generate an updated estimated data model 635 for comparison to frames 610. Any number of iterations can be employed, for example until newly-generated difference frames 645 are within a suitable threshold of difference frames 645 of a previous iteration.

Correction component 650 generates correction vectors 655 based on difference frames 645 output by the foregoing process. Correction vectors 655 may include, for each frame of frames 610, a value representing a shift in the X-direction and a value representing a shift in the Y-direction. Such values may represent a degree of registration of each frame needed to reduce tomographic inconsistency within frames 610. Due to the emphasis of the voxels of the ROI within frames 610, difference frames 645 emphasize tomographic inconsistency within the ROI to a greater extent than tomographic inconsistency within other regions. Accordingly, correction vectors 655 are biased toward to reducing tomographic inconsistency within the ROI as opposed to within other regions.

Returning to process 200, a second linear attenuation correction map is determined at S250. The coefficients of the second linear attenuation correction map may represent the actual linear attenuation coefficients of the voxels represented in the acquired frames. Attenuation correction is performed on the acquired frames at S260 using the second linear attenuation correction map. Next, and as is known in the art, a three-dimensional image is reconstructed at S270 based on the attenuation-corrected frames, the tomographic inconsistency determined at S240, and the imaging system data model. The image may then be displayed to the operator in any known format. In view of the ROI-emphasized frames used for inconsistency correction and the "true" linear attenuation coefficient map used for attenuation correction, the three-dimensional image may include usable quantitative data and exhibit improved quality within the ROI.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
    an imaging system to acquire a plurality of tomographic frames of an imaging subject, each of the plurality of tomographic frames associated with a respective projection angle; and
    a processing unit to:
    determine a region of interest of the imaging subject;
    generate a first linear attenuation coefficient map of the imaging subject, the first linear attenuation coefficient map comprising first linear attenuation coefficients associated with respective voxels of the region of interest;
    generate a second linear attenuation coefficient map of the imaging subject by increasing the values of the first linear attenuation coefficients associated with the respective voxels of the region of interest and not increasing values of linear attenuation coefficients of the first linear attenuation coefficient map associated with voxels of other regions of the imaging subject;
    attenuation-correct the plurality of tomographic frames based on the second linear attenuation coefficient map to generate a second plurality of tomographic frames;
    determine tomographic inconsistency of the second plurality of tomographic frames;
    attenuation-correct the plurality of tomographic frames based on the first linear attenuation coefficient map to generate a third plurality of tomographic frames; and
    reconstruct a three-dimensional image based on the third plurality of tomographic frames and the determined tomographic inconsistency.

2. A system according to claim 1, wherein the tomographic inconsistency is determined based on a data model of the imaging system, and wherein the three-dimensional image is reconstructed based on the third plurality of tomographic frames, the determined tomographic inconsistency of the second plurality of tomographic frames, and the data model.

3. A system according to claim 2, wherein the region of interest is determined based on the plurality of tomographic frames and on no other image data.

4. A system according to claim 3, wherein determination of the tomographic inconsistency comprises generation of shift vectors for each of the second plurality of tomographic frames, and
    wherein the three-dimensional image is reconstructed based on the third plurality of tomographic frames, the shift vectors of each of the second plurality of tomographic frames, and the data model.

5. A system according to claim 1, wherein determination of the tomographic inconsistency comprises generation of shift vectors for each of the second plurality of tomographic frames, and
    wherein the three-dimensional image is reconstructed based on the third plurality of tomographic frames, and the shift vectors of each of the second plurality of tomographic frames.

6. A system according to claim 1, wherein the region of interest is determined based on the plurality of tomographic frames and on no other image data.

7. A method comprising:
    acquiring a plurality of tomographic frames of an imaging subject;
    generating a first linear attenuation coefficient map of the imaging subject, the first linear attenuation coefficient map comprising first linear attenuation coefficients associated with respective voxels of the region of interest;
    generate a second linear attenuation coefficient map of the imaging subject by increasing the values of the first linear attenuation coefficients associated with the respective voxels of a region of interest and not increasing values of linear attenuation coefficients of the first linear attenuation coefficient map associated with voxels of other regions of the imaging subject;
    attenuation-correcting the plurality of tomographic frames based on the second linear attenuation coefficient map to generate a second plurality of tomographic frames;
    determining tomographic inconsistency of the second plurality of tomographic frames;
    attenuation-correcting the plurality of tomographic frames based on the first linear attenuation coefficient map to generate a third plurality of tomographic frames;

reconstructing a three-dimensional image based on the third plurality of tomographic frames and the determined tomographic inconsistency; and displaying the three-dimensional image.

8. A method according to claim 7, wherein the tomographic inconsistency is determined based on a data model of the imaging system, and wherein the three-dimensional image is reconstructed based on the third plurality of tomographic frames, the determined tomographic inconsistency of the second plurality of tomographic frames, and the data model.

9. A method according to claim 8, wherein determining the tomographic inconsistency comprises generating shift vectors for each of the second plurality of tomographic frames, and wherein the three-dimensional image is reconstructed based on the third plurality of tomographic frames, the shift vectors of each of the second plurality of tomographic frames, and the data model.

10. A method according to claim 7, further comprising determining the region of interest based on the plurality of tomographic frames and on no other image data.

11. A method according to claim 7, wherein determining the tomographic inconsistency comprises generating shift vectors for each of the second plurality of tomographic frames, and wherein the three-dimensional image is reconstructed based on the third plurality of tomographic frames, and the shift vectors of each of the second plurality of tomographic frames.

12. A non-transitory computer-readable medium storing program code executable by a processing unit to:

generate a first linear attenuation coefficient map of an imaging subject, the first linear attenuation coefficient map comprising first linear attenuation coefficients associated with respective voxels of the region of interest;

generate a second linear attenuation coefficient map of the imaging subject by increasing the values of the first linear attenuation coefficients associated with the respective voxels of a region of interest and not increasing values of linear attenuation coefficients of the first linear attenuation coefficient map associated with voxels of other regions of the imaging subject;

attenuation-correct a plurality of tomographic frames acquired from the imaging subject based on the second linear attenuation coefficient map to generate a second plurality of tomographic frames; and determine tomographic inconsistency of the second plurality of tomographic frames;

attenuation-correct the plurality of tomographic frames based on the first linear attenuation coefficient map to generate a third plurality of tomographic frames; and reconstruct a three-dimensional image based on the third plurality of tomographic frames and the determined tomographic inconsistency.

13. A medium according to claim 12, wherein the tomographic inconsistency is determined based on a data model of the imaging system, and wherein the three-dimensional image is reconstructed based on the third plurality of tomographic frames, the determined tomographic inconsistency of the second plurality of tomographic frames, and the data model.

14. A medium according to claim 13, the program code executable by a processing unit to:

determine the region of interest based on the plurality of tomographic frames and on no other image data.

15. A medium according to claim 14, wherein determination of the tomographic inconsistency comprises generation of shift vectors for each of the second plurality of tomographic frames, and wherein the three-dimensional image is reconstructed based on the third plurality of tomographic frames, the shift vectors of each of the second plurality of tomographic frames, and the data model.

16. A medium according to claim 12, wherein determination of the tomographic inconsistency comprises generation of shift vectors for each of the second plurality of tomographic frames, and wherein the three-dimensional image is reconstructed based on the third plurality of tomographic frames, and the shift vectors of each of the second plurality of tomographic frames.

17. A medium according to claim 12, the program code executable by a processing unit to:

determine the region of interest based on the plurality of tomographic frames and on no other image data.

* * * * *